United States Patent [19]

Miemelä et al.

[11] Patent Number: 4,707,603

[45] Date of Patent: Nov. 17, 1987

[54] PROCEDURE FOR MEASURING CONTENTS OF HYDROCARBONS IN LIQUIDS CONTAINING SUCH

[75] Inventors: Pentti Miemelä, Jääli; Jarl Jaatinen, Helsinki, both of Finland

[73] Assignee: Sahkoliikkeiden Oy, Finland

[21] Appl. No.: 817,749

[22] PCT Filed: Mar. 22, 1985

[86] PCT No.: PCT/FI85/00028

§ 371 Date: Jan. 27, 1985

§ 102(e) Date: Jan. 27, 1985

[87] PCT Pub. No.: WO85/04478

PCT Pub. Date: Oct. 10, 1985

[30] Foreign Application Priority Data

Mar. 23, 1984 [FI] Finland .................................. 841183

[51] Int. Cl.⁴ .......................................... G01N 21/35
[52] U.S. Cl. .................................... 250/339; 250/301; 250/343
[58] Field of Search ............... 250/301, 343, 339, 345, 250/346; 356/70

[56] References Cited

U.S. PATENT DOCUMENTS

| 3,732,017 | 5/1973 | Welber . | |
|---|---|---|---|
| 3,783,284 | 1/1974 | McCormack | 250/301 |
| 3,795,810 | 3/1974 | Conley et al. | 250/343 |
| 4,045,671 | 8/1977 | Dille et al. | 250/343 |
| 4,103,162 | 7/1978 | Iwamoto et al. | 250/343 |
| 4,587,427 | 5/1986 | Talbot et al. | 250/339 |

FOREIGN PATENT DOCUMENTS

| 34325 | 8/1981 | European Pat. Off. . |
| 3007453 | 9/1981 | Fed. Rep. of Germany . |
| 3208447 | 9/1982 | Fed. Rep. of Germany . |
| 2223691 | 10/1974 | France . |
| 1138711 | 1/1969 | United Kingdom . |
| 1221066 | 2/1971 | United Kingdom . |

*Primary Examiner*—Carolyn E. Fields
*Attorney, Agent, or Firm*—Steinberg & Raskin

[57] ABSTRACT

The present invention concerns a procedure for measuring the contents of hydrocarbons in liquids containing such. The liquid to be measured is conducted to a transparent measuring cuvette or equivalent and the measuring cuvette is irradiated with infrared radiation from a radiation source, and the hydrocarbon content present in the liquid is determined on the basis of the difference in absorption between the liquid together with the hydrocarbon in it and the liquid itself. In the procedure is measured the infrared absorption spectrum of the liquid containing hydrocarbons in a preselected, comparatively wide wavelength range ($\lambda_{beginning}, \lambda_{end}$) having a width exceeding that on which the absorption of the hydrocarbon being examined has an effect. The proper absorption of the liquid in the hydrocarbon's absorption range is determined by calculation with the aid of a spectral part outside said range, whereby the absorption of the hydrocarbon contained in the liquid is obtained on the basis of the difference between said absorptions.

13 Claims, 5 Drawing Figures

PROCEDURE FOR MEASURING CONTENTS OF HYDROCARBONS IN LIQUIDS CONTAINING SUCH

BACKGROUND OF THE INVENTION

The present invention concerns a procedure for measuring contents of hydrocarbons in liquids containing such, in which liquids the main component is water and which may in addition to hydrocarbons contain salts (seawater) or other dissolved chemicals (industrial emission waters). In the procedure, the liquid to be measured is conducted into a transparent measuring cuvette which is irradiated with IR radiation from a radiation source, and the contact of the hydrocarbon present in the liquid is determined on the basis of the attenuation caused by the hydrocarbon in the 3.4 to 3.5 $\mu$m wavelength range.

The IR absorption method is commonly used, for instance, in laboratory determinations of the oil content of waters. An advantage of the procedure is its universal applicability based on the fact that the absorptions of different oil types at 3.4 $\mu$m wavelength are very close to one another. Because of the strong absorption of water, it is however necessary, in laboratory measurements, to concentrate the sample before it is measured, this being accomplished by extracting the oil in carbon tetrachloride and separating from the water the extract thus obtained. As a consequence, the procedure is slow and introduces a risk of toxic emissions.

In a procedure known in the prior art, the absorption of water is compensated for by forming, from the sample proper, a reference sample from which the oil has been removed. When these two are pumped through the cuvette in alternation, the attenuation due to the oil can be measured. In order to achieve sufficient measuring accuracy, the differential temperature between the samples is equalized prior to the cuvette with the aid of a heat exchanger, and for eliminating the differential pressure, they are always stopped in the cuvette for the duration of measurement. To produce the reference sample, an ultrafilter is employed, which removes, on the side of the oil, any solid particles which may occur therein. The attenuation caused by these is compensated by using, in addition to the measuring wavelength, another wavelength at which the oil effects no absorption. The procedure combines the accuracy and reliability of the laboratory method and the advantage of high measuring speed. Its hydraulics part is, however, still complicated, comprising an ultrafilter, a pipe line for the reference sample, pumping means for the reference liquid and a heat exchanger.

SUMMARY OF THE INVENTION

The object of the invention is to provide an improvement in the measuring methods known in the art. A more detailed aim of the invention is to provide a procedure in which the sample processing involved in the measuring procedure known in the art can be substantially simplified. The other aims of the invention, and the advantages to be gained therewith, are readable in the disclosure of the invention.

The aims of the invention are achieved by means of a procedure which is mainly characterized in that the infra-red absorption spectrum of the liquid containing hydrocarbons is measured in a preselected wavelength range of relatively great width, the width of this wavelength range exceeding that of the range in which the absorption of the hydrocarbon under investigation has an effect, and that the proper absorption of the liquid, in the hydrocarbon absorption range, is determined by calculation with the aid of the spectral part outside said range, whereby the absorption of the hydrocarbon in the liquid is obtained on the basis of the difference between said absorptions.

By the procedure of the invention, numerous remarkable advantages are gained. The procedure of the invention allows the hydraulics component required in the measurement to be substantially simplified. Hereby, it is possible to omit, for instance, the ultrafilter inserted in the liquid flow line, the reference liquid pipe line going to the measuring cuvette, the reference liquid pumping means required in said pipe line, and the heat exchanger.

BRIEF DESCRIPTION OF THE DRAWINGS

The invention is described in detail by referring to certain advantageous embodiments of the invention presented in the figures of the drawings attached, but to which the invention is not meant to be exclusively confined.

DESCRIPTION OF THE PREFERRED EMBODIMENTS

Figure 1:
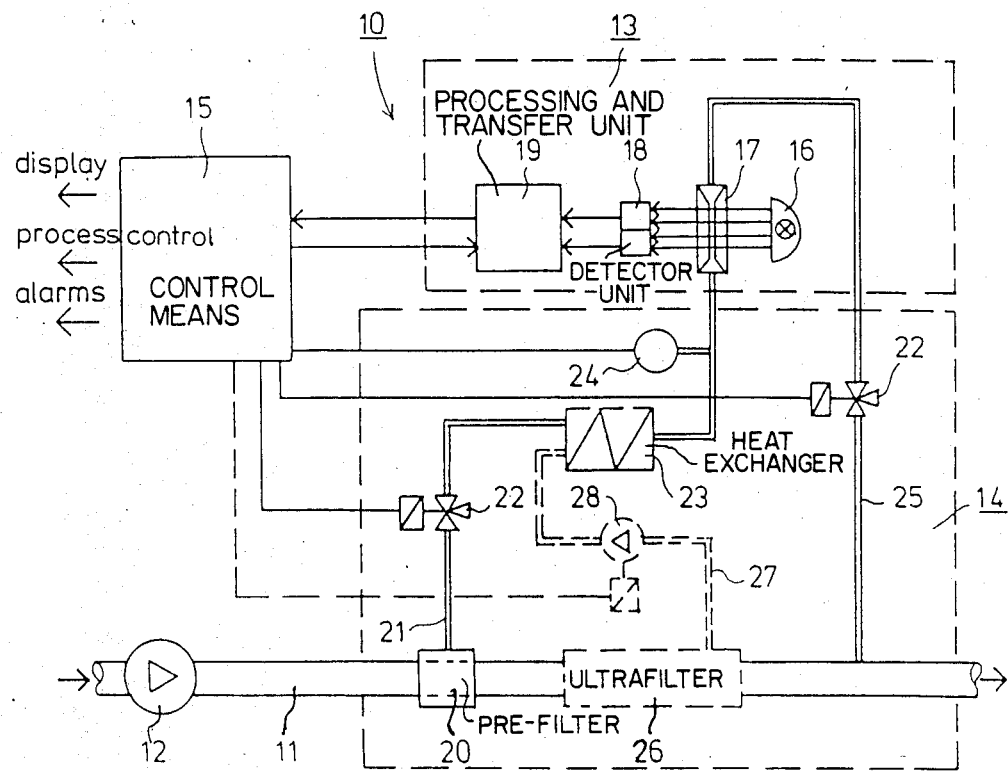
FIG. 1 presents in block diagram form the principle of the procedure of the invention, in which are indicated by interrupted lines the components of the hydraulics part included in procedures of prior art and which are superfluous in the procedure of the invention.

In the embodiment of FIG. 1, the measuring apparatus used in the measuring procedure of the invention has in general been indicated by reference numeral 10. The measuring apparatus 10 comprises a measuring unit part 13 and a hydraulics part 14, and a control part 15. With the measuring apparatus 10 is measured the content of the hydrocarbon, or hydrocarbons, present in the liquid flowing in the pipe line 11, e.g. the content of oil. The transfer pump and homogenizer in the liquid line 11 are indicated by reference numeral 12.

The measuring unit part 13 comprises an IR source 16, a measuring cuvette 17 or a corresponding transparent pipe length, a detector unit 18, in FIG. 1 depicted as a two-channel detector, and a processing and transfer unit 19 for the measuring signals.

The hydraulics part 14 comprises a pre-filter 20, a pipe line 21 leading to the measuring cuvette 17, sample and flushing valves 22, a heat exchanger 23, and a pressure transducer 24. By reference numeral 25 is indicated the discharge line along which the measured liquid is conducted from the measuring cuvette 17 to the liquid line 11. For flushing, pure liquid may be used, which is conducted through the valves 22 into the measuring cuvette 17. It is possible to use either pure water or a suitable solvent for flushing.

In the measuring system presented in FIG. 1 are indicated by interrupted lines the ultrafilter 26 for the reference liquid, the pipe line 27 along which the reference liquid is conducted to the measuring cuvette 17, and the reference liquid pumping means 28 in the pipe line 27. In the procedure of the invention, the hydraulics part 14 can be simplified so that the part 23,26,27 and 28 used in the procedures of prior art may be omitted altogether.

Figure 2:
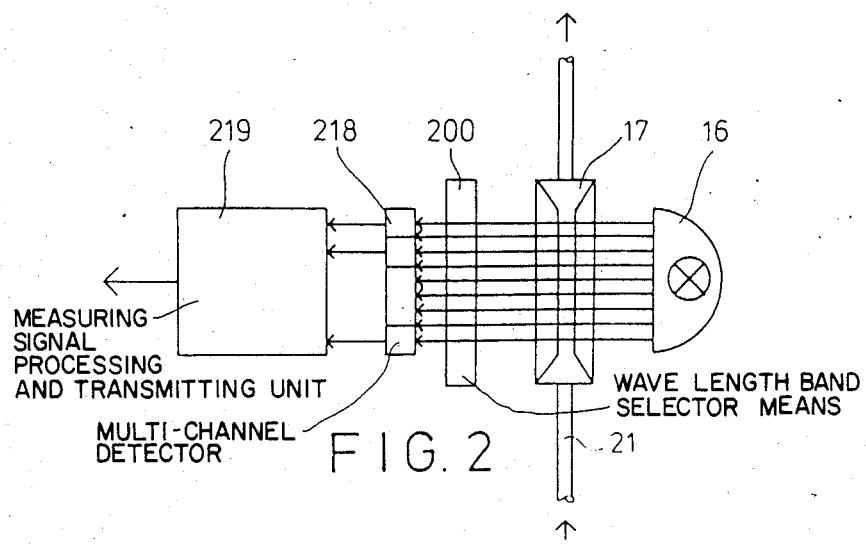
FIG. 2 presents in block diagram form an advantageous embodiment of the measuring unit presented in FIG. 1.

In FIG. 2 is presented an advantageous embodiment of the measuring unit part 13 presented in FIG. 1. The measurement in accordance with FIG. 2 is based on so-called multi-colour measurement. In this embodiment. The IR source is indicated by reference numeral 16, the measuring cuvette by reference numeral 17 and the pipe line leading to the measuring cuvette by reference numeral 21, as in FIG. 1. In the present embodiment, for the detector unit is used a multi-channel detector 218, before which has been disposed a wavelength band selector means 200. The reference numeral 219 indicates the measuring signal processing and transmitting unit. It is thus understood that, in multi-colour measurement, a wide band source is used and the measuring head contains a plurality of parallel channels. It is easy to provide four channels with a multi-colour detector (each element has separate filters). Even more numerous channels can be implemented by using a line of detectors and a dispersive element, such as e.g. a grating or prism.

Figure 3:
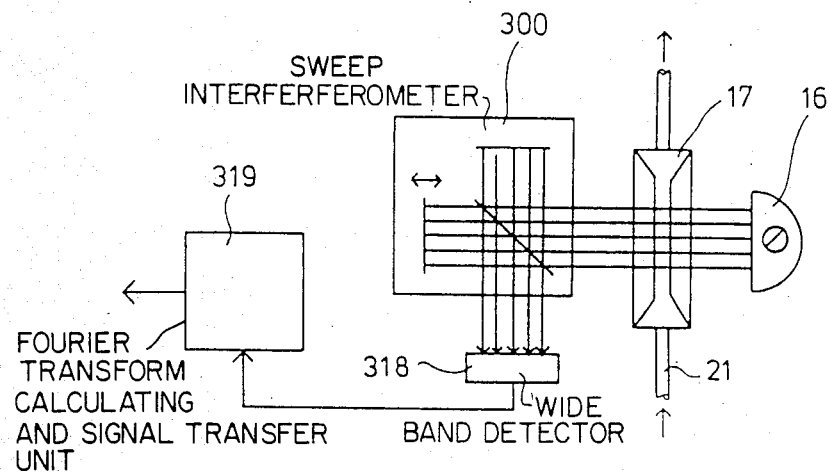
FIG. 3 presents in block diagram form another advantageous embodiment of the measuring unit presented in FIG. 1.

In FIG. 3 is presented another advantageous embodiment of the measuring unit part 13 shown in FIG. 3. This embodiment is based on a so-called Fourier spectrometer. In this embodiment, reference numeral 16 indicates the IR source, reference numeral 17 the measuring cuvette, and reference numeral 21 the pipe line leading to the measuring cuvette 17, as in FIG. 1. In this embodiment is used a wide-band detector 318, to which the radiation in the IR range passing through the measuring cuvette 17 is conducted with the aid of a sweep interferometer 300. By reference numeral 319 is indicated the Fourier transform calculating, and signal transfer unit. Thus, in the Fourier spectrometer is used a wide band-source, and a central part is the sweeping interferometer. The spectrum is established by calculation.

Figure 4:
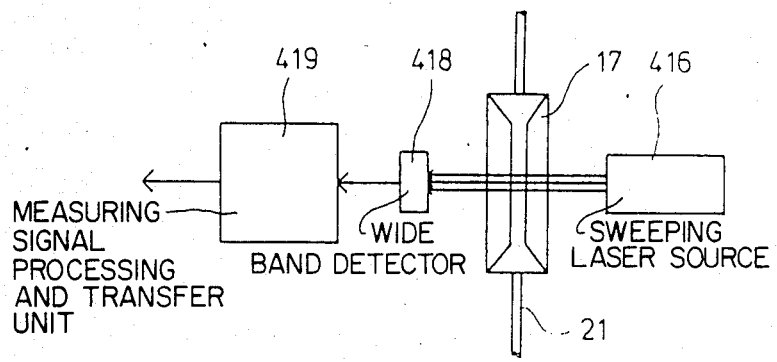
FIG. 4 presents in block diagram form a third advantageous embodiment of the measuring unit shown in FIG. 1.

In FIG. 4 is presented a third advantageous embodiment of the measuring unit part 13 shown in FIG. 1. This embodiment is based on a laser spectrometer. By reference numeral 17 is indicated the measuring cuvette and by reference numeral 21, the pipe line leading to the measuring cuvette 17, as in FIG. 1. In this embodiment is used a sweeping laser source 416 and, for detector, a wide-band detector 418. The reference numeral 419 indicates the measuring signal processing and transfer unit. It is thus understood that in the laser spectrometer is used a tunable laser source and a wide-band detector.

The control means 15, presented in FIG. 1, provides the display, process controls and alarms. The calculation of measuring results is carried out by a microcomputer, whereby real time processing becomes feasible and a precise algorithm is obtained e.g. for calculating the absorption of water.

Figure 5:
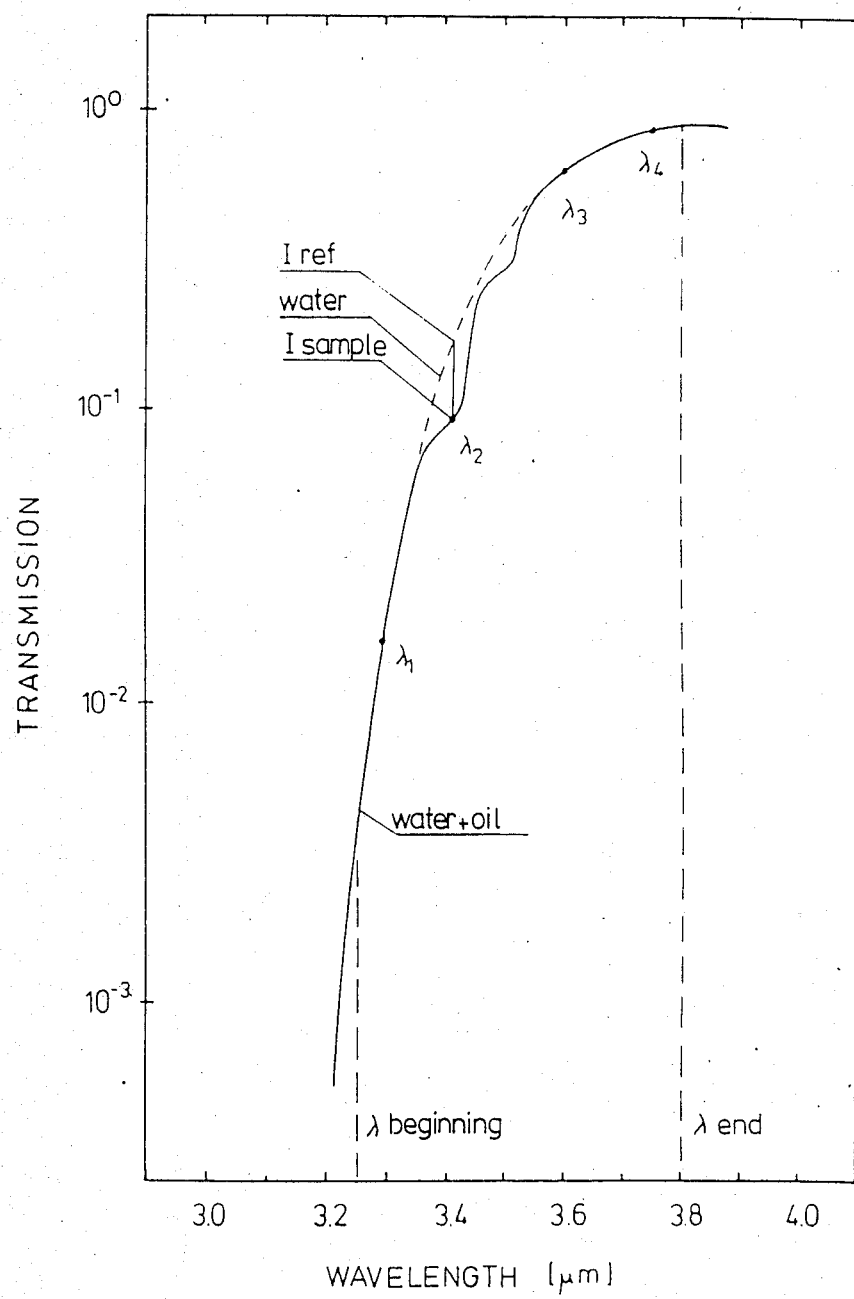
FIG. 5 presents graphically the absorption graph of oil-containing water, plotted over the wavelength, the absorption graph of water having been entered in the figure with interrupted lines.

In FIG. 5 is graphically presented the absorption graph for water containing oil. The absorption graph of water has been entered as an interrupted line. The wavelength range pre-selected in the procedure of the invention is entered in FIG. 5 on the interval $\lambda_{beginning}$ to $\lambda_{end}$. In FIG. 5 is shown one possibility of selecting the measuring wavelengths (4-colour measurement) $\lambda_1=3.30$ μm, $\lambda_2=3.42$ μm, $\lambda_3=3.60$ μm and $\lambda_4=3.75$ μm. In the present instance, oil affects the intensity value $I_{sample}$ at wavelength $\lambda_2$. The intensity value $I_{ref}$ of oil-free water can be determined by calculation from the intensity values at wavelengths $\lambda_1$, $\lambda_3$ and $\lambda_4$, and the absorption of oil is thus obtained as the difference of the intensity values of sample and reference. By using a greater number of measuring wavelengths, the accuracy and reliability of the measurements can be improved. By sweeping methods it is even possible to determine the integral of oil induced absorption over the wavelength range concerned.

The procedure of the invention has remarkable advantages. The measurement is made directly from the water sample, and no complex arrangements are needed for processing the sample. The effect of such substances present in the water is eliminated from the measurement which give rise to uniform attenuation in the wavelength range in question. Such are, for instance, solid particles causing turbidity, and certain salts dissolved in the water. It is possible to measure by the procedure, in addition to oil, also some other hydrocarbons admixed to water.

I claim:

1. Method for measuring hydrocarbon content in liquid containing the same, comprising the steps of
    conducting the liquid to be measured into a transparent measuring cuvette,
    irradiating the cuvette with infrared radiation of of wavelengths within a first wide wavelength range whereby the liquid absorbs infrared rays over the first wide range which is greater than a second narrow wavelength range over which the hydrocarbon affects the infrared absorption of the liquid,
    measuring the infrared absorption spectrum of the liquid over the first wide range,
    determining infrared absorption of the liquid without the hydrocarbon in the second range by extrapolating the absorption spectrum for the liquid without the hydrocarbon based upon the measurement of infrared absorption spectrum outside the second wavelength range, and
    determining an indication of the content of the hydrocarbon in the liquid as a difference between the measured infrared absorption spectrum of the liquid with the hydrocarbon and the extrapolated infrared absorption spectrum of the liquid without the hydrocarbon in the second wavelength range.

2. The method of claim 5, wherein at least four measurements of the infrared absorption spectrum of the liquid are made over the first range.

3. The method of claim 2, wherein at least two of the measurements are outside the second range.

4. The method of claim 3, wherein at least 3 of the measurements are outside the second range.

5. The method of claim 4, wherein the liquid is water.

6. The method of claim 5, wherein the measurements are taken over a wave length range of about 3.3–3.8 microns.

7. The method of claim 6, wherein the measurements are taken at wavelengths of about 3.3, about 3.42, about 3.6, and about 3.75 microns.

8. The method of claim 1, wherein the measuring carried out is a multi-color measurement utilizing a multichannel detector and a wavelength band selector between the detector and the cuvette.

9. The method of claim 1, wherein the measuring carried out is a Fourier spectrometer measurement utilizing a wide-band detector and a sweeping interferometer through which radiation from the cuvette is conducted to the detector.

10. The method of claim 1, wherein the measuring carried out is a laser spectrometer measurement utilizing a sweeping laser radiation source and a wide-band detector.

11. The method of claim 1, wherein need to generate a reference sample of liquid without hydrocarbon therein is eliminated.

12. The method of claim 1, wherein filtering of the liquid to generate a reference sample is eliminated.

13. The method of claim 1, comprising the additional step of
  determining an integral of hydrocarbon-induced absorption by taking a sweep of measurements over the first and second ranges.

* * * * *